United States Patent [19]

Hammen et al.

[11] Patent Number: 4,636,503

[45] Date of Patent: Jan. 13, 1987

[54] DUST-FREE QUINOXALINE 1,4-DI-N-OXIDES

[75] Inventors: Hans W. Hammen, Solingen; Herbert Voege, Leverkusen, both of Fed. Rep. of Germany

[73] Assignee: Bayer Aktiengesellschaft, Leverkusen, Fed. Rep. of Germany

[21] Appl. No.: 667,652

[22] Filed: Nov. 2, 1984

[30] Foreign Application Priority Data

Nov. 11, 1983 [DE] Fed. Rep. of Germany ....... 3340931

[51] Int. Cl.$^4$ ............................................. A61K 31/50
[52] U.S. Cl. .................................................... 514/249
[58] Field of Search ......................................... 514/249

[56] References Cited

FOREIGN PATENT DOCUMENTS

| 1670935 | 2/1971 | Fed. Rep. of Germany. |
| 2639429 | 3/1978 | Fed. Rep. of Germany ...... 514/249 |
| 2076819 | 12/1981 | United Kingdom ................ 514/249 |

*Primary Examiner*—Frederick E. Waddell
*Attorney, Agent, or Firm*—Sprung, Horn, Kramer & Woods

[57] ABSTRACT

Quinoxaline 1,4-di-N-oxides are rendered non-dusting by adjusting their water content to about 3–20% by weight and adding thereto about 2–20% by weight of a flow-regulating agent such as silica. The compositions can be added to animal feeds.

4 Claims, No Drawings

DUST-FREE QUINOXALINE 1,4-DI-N-OXIDES

The invention relates to dust-free quinoxaline 1,4-di-N-oxides, their preparation and their use in premixes and feed additives in livestock rearing.

Quinoxaline 1,4-di-N-oxides, in particular 2-methyl-3-carboxamidoquinoxaline 1,4-di-N-oxides and 3-[N-(2-hydroxyethyl)carbamoyl]-2-methylquinoxaline 1,4-di-N-oxide, and processes for their preparation are disclosed in German Patent Specification No. 1,670,935. These compounds have valuable chemotherapeutic and growth-promoting effects in livestock rearing.

In the preparation processes, quinoxaline 1,4-di-N-oxides result as solid, crystalline or amorphous, substances which tend to form dusts. Active compounds in the form of dust, or active compounds which show a tendency to form dusts, cause difficulties in the preparation of premixes or final formulations, for example final feeds for livestock rearing.

In addition, it is not desirable to mix products which contain active compound dust which can be inhaled, even if a health hazard is not immediately perceptible.

Dust-free quinoxaline 1,4-di-N-oxides are also interesting for reasons of industrial safety. Quinoxaline 1,4-di-N-oxides tend to deflagrate or explode. They deflagrate even when air is excluded.

A hazard of this type is reduced by the absence of dust, in particular in the premixes. However, the addition of water prevents, even in the pure substance, the propagation of an explosion, since the energy necessary for propagation is absorbed by evaporation of the water. A product of this type, which is no longer explosive, can then be transported even, for example, by air freight.

The invention relates to a process for the preparation of dust-free quinoxaline 1,4-di-N-oxides, which comprises (a) drying the quinoxaline 1,4-di-N-oxides, which have been prepared by customary processes and precipitated out, crystalline or amorphous, from a reaction mixture containing water and are moist from the filter, in such a manner that their water content is 3-20% by weight, or, in the case where the quinoxaline 1,4-di-N-oxides have been prepared in an anhydrous or virtually anhydrous system, after the latter have been isolated from the reaction mixture, water is added to them in an amout such that their water content is 3-20% by weight, and (b) adding 2-20% by weight of a flow-regulating agent to these quinoxalin 1,4-di-N-oxides which are moist with water.

The process is distinguished by the proportion of water which is left behind in or added to the filter cake of the active compound preferably being 5-15%, and the latter being then mixed with 2-20%, preferably 5-15%, of a flow-regulating agent. The latter can be carried out both in the batch process and continuously during discharge. It is also possible to combine a milling process with the mixing.

Since the quinoxaline 1,4-di-N-oxides containing the indicated amount of water might form lumps during the period of storage, it is necessary to add to the active compounds another auxiliary which prevents this and keeps the active compound crystals or particles non-compacted and separated. Otherwise, the preparation of a homogeneous premix or final feed is possible only by employing an additional milling process.

The substances which can be used as flow-regulating agents are those which are able to bind a certain amount of water. In this context, the best known substances to be mentioned are colloidal and precipitated silica, but also usable are kieselgur, light calcium phosphate or calcium sulphate which has been prepared by specific processes to be water-adsorbing, natural and synthetic zeolites, for example bentonites, and also clays amongst others. Of the organic flow-regulationg agents, cross-linked polymers which are able to absorb large amounts of water while swelling should be particularly mentioned. These can originate from all areas of polymer chemistry, for example crosslinked acrylates, methacrylates, polyamides and polyvinylpyrrolidones. Cellulose derivatives, including natural products, and, for example, starches, can also be of interest. In addition, it is also possible to add preservatives, such as, for example, esters of p-hydroxybenzoic acid or propionic acid, sorbic acid or its salts.

The invention also relates to the use of the quinoxaline 1,4-di-N-oxides according to the invention in livestock rearing.

The quinoxaline 1,4-di-N-oxides can be used in all areas of livestock rearing as agents for promoting and accelerating growth and for impoving the feed utilization of healthy and sick livestock.

In this connection, the efficacy of the quinoxaline 1,4-di-N-oxides is essentially independent of the species and the sex of the livestock. The quinoxaline 1,4-di-N-oxides prove to be particularly useful for the rearing and maintenance of young and fattening livestock.

Examples of livestock for which the quinoxaline 1,4-di-N-oxides can be used to promote and accelerate growth and to improve the feed utilization which may be mentioned are the following useful and ornamental livestock:

Warm-blooded species, such as cattle, pigs, horses, sheep, goats, cats, dog, rabbits, fur-bearing animals, for example mink, and chinchilla, poultry, for example chickens, geese, ducks, turkeys, pigeons, parrots and canaries, and cold-blooded species, such as fish, for example carp, and reptiles, for example snakes.

Because of the favorable properties of the active compounds, the amounts of the quinoxaline 1,4-di-N-oxides which are administered to the livestock to achieve the desired effect can be varied over a wide range. They are preferably about 0.01 to 50, in particular 0.1 to 10, mg kg of body weight per day. The duration of administration can be from a few hours or days up to several years. The appropriate amount of the quinoxaline 1,4-di-N-oxides and the appropriate duration of aministration depend, in particular, on the species, the age, the sex, the state of health and the method of maintaining and feeding the livestock, and they can be readily determined by all those skilled in the art.

The quinoxaline 1,4-di-N-oxides are admininstered to the livestock by the customary methods. The method of administration depends, in particular, on the species, the behavior and the state of health of the livestock. Thus, the administration can be carried out orally or parenterally, once or several times a day, at regular or irregular intervals.

For reasons of convenience, in most cases oral administration, in particular in the rhythm of the intake of feed and/or drink by the livestock, is to be preferred.

The quinoxaline 1,4-di-N-oxides can be administered as a mixture of the pure substances or in a formulated form, that is to say mixed wit inert, non-toxic vehicles of any desired type, for example with vehicles and in formulations as are customary for nutritive preparations.

The quinoxaline 1,4-di-N-oxides are administered in a suitable form, where appropriate in the formulated form together with pharmaceutical active compounds, mineral salts, trace elements, vitamins, proteins, lipids, colorants and/or flavorings.

Oral administration together with the feed and/or drinking water is advisable, the quinoxaline 1,4-di-N-oxides being added as required to the total amount or to only parts of the feed and/or the drinking water.

The quinoxaline 1,4-di-N-oxides are added to the feed and/or drinking water by customary methods, by simply mixing as the mixture of pure substances, preferably in the finely divided form, or in a formulated form mixed with edible, non-toxic vehicles, where appropriate in the form of premixes, to which the invention also relates, or a feed concentrate.

The feed and/or drinking water can, for example, contain the quinoxaline 1,4-di-N-oxides in a weight concentration of about 5–500 ppm, in particular 10–300 ppm. The optimal level of the concentration of quinoxaline 1,4-di-N-oxides in the feed and/or drinking water depends, in particular, on the amount of the feed and/or drinking water consumed by the livestock, and these can be readily determined by all those skilled in the art.

The type of the feed and its composition has no relevance in this context. All conventional or special feed compositions which preferably contain the customary balance of energy carriers and builders necessary for a balanced diet, including vitamins and minerals, can be used. The feed can be composed of, for example, plant materials, for example hay, beets, cereals, cereal by-products, animal materials, for example meat, lipids, bonemeal, fish products, vitamins, for example vitamin A, D complex and B complex, proteins, aminoacids, for example DL-methionine, and inorganic materials, for example lime and sodium chloride.

Feed concentrates contain the quinoxaline 1,4-di-N-oxides in addition to edible materials, for example ryemeal, corn meal, soy bean meal or lime, where appropriate with other nutrients and builders, and proteins, mineral salts and vitamins. They can be prepared by the customary mixing methods.

EXAMPLE 910 kg of 3-[N-(2-hydroxyethyl)carbamoyl]-2-methylquinoxaline 1,4-di-N-oxide with a residual moisture of 10% (=819 kg of 100% active compound +91 kg of water) and 90 kg of silica are introduced into a mixer and mixed until homogeneous. The free-flowing mixture is discharged into drums. It contains 81.9% of active compound, 9.1% of water and 9% of silica.

Demonstration of the safety compared with pure active compound.

In two dishes behind safety glass, the pure substance in the first test, and the mixture according to the above preparation example in the second test, is touched with a glowing wire. In the first test, the entire amount of substance deflagrates with the formation of black smoke.

In the second test, the substance ignites at the point of contact, but there is no propagation of the deflagration and it is immediately extinguished.

It will be understood that the specification and examples are illustrative but not limitative of the present invention and that other embodiments within the spirit and scoped of the invention wil suggest themselves to those skilled in the art.

What is claimed is:

1. A process for the preparation of a dust-free animal growth-promoting quinoxaline 1,4-di-N-oxide comprising
   (a) adjusting the water content of the quinoxaline 1,4-di-N-oxide to about 5–15% by weight, and
   (b) adding thereto a water-binding flow-regulating agent in an amount approximately equal to the water content.

2. A process according to claim 1, wherein the quinoxaline 1,4-di-N-oxide is a moist filter cake.

3. A process according to claim 1, wherein the quinoxaline 1,4-di-N-oxide is produced under substantially annhydrous conditions and the adjustment of the water content is effected by addition of water thereto.

4. A process according to claim 1, wherein the flow-regulating agent is selected from the group consisting of silica, kieselgur, calcium phosphate, calcium sulphate, zeolite, clay, cross-linked acrylate, methacrylate, polyamide or polyvinylpyrrolidone, cellulose derivative and starch.

* * * * *